United States Patent
Puvvada et al.

(10) Patent No.: US 6,664,217 B1
(45) Date of Patent: Dec. 16, 2003

(54) TOILET BAR HAVING SIMULTANEOUS EXFOLIATING AND MOISTURIZING PROPERTIES

(75) Inventors: Sudhakar Puvvada, Shelton, CT (US); Albert Joseph Post, Orange, CT (US); Krishna Kumar Subramanyan, Clifton, NJ (US); Anthony William Johnson, Fairfield, CT (US); Craig Stephen Slavtcheff, Guilford, CT (US); Adolf Peter Barth, Buxtehude (DE); Petra Meinschien, Hamburg (DE)

(73) Assignee: Unilever Home & Personal Care, USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 10/198,421

(22) Filed: Jul. 18, 2002

(51) Int. Cl.$^7$ .................................................. A61K 7/50
(52) U.S. Cl. ........................ 510/141; 510/148; 510/152; 510/155; 510/156
(58) Field of Search ................................. 510/141, 148, 510/152, 155, 156

(56) References Cited

U.S. PATENT DOCUMENTS

| | | |
|---|---|---|
| 5,914,133 A | 6/1999 | Tsujino |
| 6,074,998 A | 6/2000 | He et al. |
| 6,342,470 B1 | 1/2002 | Aronson et al. |
| 6,376,441 B1 | 4/2002 | Ross et al. |
| 6,384,000 B1 | 5/2002 | McFann et al. |
| 6,403,543 B1 * | 6/2002 | George .................... 510/147 |

* cited by examiner

Primary Examiner—Necholus Ogden
(74) Attorney, Agent, or Firm—Alan A. Bornstein

(57) ABSTRACT

Mild toilet bar compositions are described that contain synthetic surfactants, moisturizers and exfoliant particles where 25% or more of the particles have a major axis length of between 100 and 600 microns. The combination of the mild surfactants, moisturizers, and exfoliants provide the user with simultaneous moisturization and exfoliation.

17 Claims, No Drawings

TOILET BAR HAVING SIMULTANEOUS EXFOLIATING AND MOISTURIZING PROPERTIES

BACKGROUND OF THE INVENTION

1. Field of the Invention

The present invention relates to a toilet bar suitable for topical application for cleansing the human body, such as the skin and hair. In particular, it relates to a toilet bar composition that is mild to the skin and which also exfoliates the skin.

2. The Related Art

Exfoliating toilet bars are well known. However, the majority of them are very irritating to the skin due to the fact that they are soap based, have high levels of harsh or marginally effective exfoliants, low levels of moisturizers, or some combination of the preceding. Certain prior art toilet bars with high levels of mild synthetic surfactants ("Syndet") and high levels of moisturizers have been described as optionally having exfoliant particles or beads such as sic polyoxyethylene (polyethylene) beads, walnut shells, and apricot seeds, and the like. See e.g. U.S. Pat. No. 6,376,441; U.S. Pat. No. 6,342,470; U.S. Pat. No. 6,384,000; and U.S. Pat. No. 6,074,998. Surprisingly it has been found that mild toilet bars having one or more syndet surfactants, one or more moisturizers, and exfoliants of a specific particle size range provide the user with enhanced moisturization and exfoliation simultaneously. This causes the user's exfoliated skin to appear fresh and healthy as it removes the dull layer of dead skin, accompanied with deep cleansing leading to less clogged pores while at the same time moisturizing the skin to minimize irritation and dryness as shown by various art recongnized techniques described below.

While not wishing to be bound by the following skin treatment theories, Applicants believe that exfoliation improves skin cleansing by helping to mechanically remove dirt and oil from the skin. Exfoliation also is believed to aid the process of desquamation. Desquamation is a natural process by which corneocytes are removed from the stratum corneum, which is the top layer of skin cells. Corneocytes are simply the cells that comprise the stratum corneum, and they are constantly being removed as the skin regenerates. Exfoliation aids in removing the flaky corneocytes that are ready to detach from the stratum corneum, and so promotes smoother, less flaky skin.

Other potential health benefits to exfoliation in addition to improved scale (flake) removal and oil removal, as suggested above, are reduction in bacteria on the skin, and increased blood flow to the skin due to the mechanical stimulation.

The inventive bar under actual use conditions is expected to show improvements in skin softness, skin smoothness, and similar consumer perceived benefits such as exfoliation efficiency, mildness, moisturization efficiency, deposition efficiency, cleansing efficiency, and a bar property such as skin abrasiveness, etc. based on changes from the baseline for these measurements using toilet bars without the inventive composition as quantified using the test methods described below.

SUMMARY OF THE INVENTION

In one aspect the present invention is a toilet bar, having:
a) a cleansing base including about 20 to 60% by wt. of one or more Syndet surfactants;
b) about 10 to 50% by wt. of a moisturizer; and
c) exfoliant particles wherein at least 25% by wt. of the particles have a particle size dimension along the major axis of the particle of from about 100 microns to about 600 microns.

In another aspect of the invention is a toilet bar made by a process including the steps of:
  (a) providing at least one synthetic surfactant, at least one moisturizer, and at least one exfoliant;
  (b) mixing the ingredients of step (a) to form a product preblend, at or above a temperature sufficient to render the preblend flowable, until the preblend is substantially uniform, wherein the exfoliant, and a substantial portion of the at least one or more moisturizers is excluded from the preblend;
  (c) cooling the resulting product preblend;
  (d) optionally milling or refining the cooled product preblend to form pellets;
  (e) blending the exfoliant with the substantial portion of one or more of the moisturizers not added to the product preblend formed in step (b) or (c) to form an exfoliant preblend;
  (f) mixing the exfoliant preblend with the cooled product preblend in a solids blending device;
  (g) refining the product of step (f) at least once; and
  (h) extruding and stamping the product into toilet bars.

In another aspect of the invention is a method for simultaneously exfoliating and moisturizing the skin comprising the steps of:
  a) providing a bar including
    i) a cleansing base including about 20 to 60% by wt. of one or more Syndet surfactants;
    ii) about 10 to 50% of a moisturizer; and
    iii) exfoliant particles wherein at least 25% by wt. of the particles have a particle size dimension along the major axis of the particle of from about 100 microns to about 600 microns;
  b) adding sufficient water to wet the bar and the skin;
  c) applying the bar to the skin;
  d) rubbing the bar onto the skin for a time sufficient to remove dead skin cells and coat the underlying skin with at least one moisturizer.

In a further aspect of the invention is a method for providing the user with a variable level of exfoliation and moisturization on different regions of the body, including the steps of:
  (a) providing a toilet bar, wherein the bar includes
    1. a cleansing base including about 20 to 60% by wt. of one or more Syndet surfactants;
    2. about 10 to 50% of a moisturizer; and
    3. exfoliant particles wherein at least 25% by wt. of the particles have a particle size dimension along the major axis of the particle of from about 100 microns to about 600 microns;
  (b) moistening the bar; the body or both;
  (c) rubbing the bar on user selected areas of the skin for a time sufficient to remove dead skin cells where substantial exfoliation is desired;
  (d) adding sufficient water to the bar to form a lather;
  (e) rubbing the lather onto user selected areas of the skin where moisturization without substantial exfoliation is desired for a time sufficient to coat the underlying skin with at least one moisturizer; and,
  (f) wherein steps (c) to (e) may be carried out in any sequence by the user.

DETAILED DESCRIPTION OF THE INVENTION:

In one aspect of the present invention is a toilet bar, having:
 (a) a cleansing base, preferably having a zein value of less than 50, 40, 30, or 25; the cleansing base including about 20 to 60%; preferably 25 to 55% by wt. of one or more Syndet surfactants;
 (b) about 10 to 50%; preferably 20 to 45% by wt. of a moisturizer; and
 (c) exfoliant particles wherein at least 25% by wt., preferably at least 50%; of the particles have a particle size dimension along the major axis of the particle of from about 100 microns to about 600 microns; preferably about 100 to 300 microns, and more preferably where the smallest particle in the above weight fraction is 150 microns.

Advantageously, the exfoliant particles have a hardness of less than about 4 Mohs, preferably less than about 3 Mohs. Preferably the exfoliant particles have a color distinct from the cleansing base. Advantageously the inventive bar has a sensory exfoliation index less than or equal to 10, preferably less than or equal to 5, more preferably less than or equal to 3; using the test method defined below. Exfoliant particles are preferably present in the inventive bar at a concentration level of less than about 1%, preferably less than 0.5% by wt. Exfoliant particles greater than 400 microns, preferably 300 microns, are advantageously at a concentration level of less than about 0.25%, preferably less than about 0.05%; and more preferably less than about 0.025% by wt.

Exfoliant particles may advantageously be selected from polyethylene, microcrystalline wax, jojoba esters, amorphous silica, talc, tricalcium orthophosphate, or blends thereof, and the like; preferably polyethylene, microcrystalline wax, jojoba esters.

The inventive bar also contains moisturizers preferably selected from fatty acids, triglycerides, mineral oil, petrolatum, glycerin, polyethylene glycol, or blends thereof and the like; more preferably selected from fatty acids, triglycerides, and most preferably stearic acid, sunflower seed oil. Advantageously the moisturizer to exfoliant ratio is in the range of about 20:1 to 500:1; preferably about 100:1 to 500.

With respect to pH, the inventive bar advantageously provides an aqueous slurry pH of about 4 to 8, preferably about 6 to 8 and preferably includes less than about 10%, preferably less than about 3%, by wt. of soluble soap as defined below.

In another aspect of the invention is a toilet bar made by a process including the steps of:
 (a) providing at least one synthetic surfactant, at least one moisturizer, and at least one exfoliant;
 (b) mixing the ingredients of step (a) to form a product preblend, at or above a temperature (preferably above 85 C) sufficient to render the preblend flowable, until the preblend is substantially uniform (preferably for about 30 minutes to 1 hour and 30 minutes), wherein the exfoliant, (optionally a fragrance), and a substantial portion of the at least one or more moisturizers is excluded from the preblend (preferably the amount of excluded moisturizer is less than about 5% by weight of the formula, preferably less than about 2% by weight of the formula);
 (c) cooling the resulting product preblend (preferably using a chill roll or the like);
 (d) optionally milling or refining the cooled product preblend to form pellets;
 (e) blending the exfoliant with the substantial portion of one or more of the moisturizers not added to the product preblend formed in step (b) or (c) to form an exfoliant preblend (preferably the remaining moisturizer component is in liquid form or is liquified with heating);
 (f) mixing the exfoliant preblend with the cooled product preblend in a solids blending device (preferably a ribbon blade mixer, refiner, and z blade mixer and the like);
 (g) refining the product of step (f) at least once; and
 (h) extruding and stamping the product into toilet bars.

Preferably the step of blending a fragrance is done either simultaneously with the exfoliant and moisturizer or as a separate step to form the exfoliant preblend.

In another aspect of the invention is a method for simultaneously exfoliating and moisturizing the skin comprising the steps of:
 (a) providing a bar including
  i) a cleansing base, preferably having a zein value of less than 50, 40, 30, or 25; the cleansing base including about 20 to 60%; preferably 25 to 55% by wt. of one or more Syndet surfactants;
  ii) about 10 to 50%; preferably 20 to 45% by wt. of a moisturizer; and
  iii) exfoliant particles wherein at least 25% by wt., preferably at least 50%; of the particles have a particle size dimension along the major axis of the particle of from about 100 microns to about 600 microns; preferably about 100 to 300 microns, and more preferably where the smallest particle in the above weight fraction is 150 microns.
  iv) Adding sufficient water to wet the bar and the skin;
  v) applying the bar to the skin;
  vi) rubbing the bar onto the skin for a time sufficient to remove dead skin cells and coat the underlying skin with at least one moisturizer.

In a further aspect of the invention is a method for providing the user with a variable level of exfoliation and moisturization on different regions of the body, including the steps of:
 a) providing a toilet bar, wherein the bar includes
  i) a cleansing base, preferably having a zein value of less than 50, 40, 30, or 25; the cleansing base including about 20 to 60%; preferably 25 to 55% by wt. of one or more Syndet surfactants;
  ii) about 10 to 50%; preferably 20 to 45% by wt. of a moisturizer; and
  iii) exfoliant particles wherein at least 25% by wt., preferably at least 50%; of the particles have a particle size dimension along the major axis of the particle of from about 100 microns to about 600 microns; preferably about 100 to 300 microns, and more preferably where the smallest particle in the above weight fraction is 150 microns.
 b) moistening the bar; the body or both;
 c) rubbing the bar on user selected areas of the skin for a time sufficient to remove dead skin cells where substantial exfoliation is desired;
 d) adding sufficient water to the bar to form a lather;
 e) rubbing the lather onto user selected areas of the skin where moisturization without substantial exfoliation is desired for a time sufficient to coat the underlying skin with at least one moisturizer; and,
 f) wherein steps (c) to (e) may be carried out in any sequence by the user.

The inventive bar under actual use conditions is expected to show improvements in skin softness, skin smoothness, and similar consumer perceived benefits such as exfoliation efficiency, mildness, moisturization efficiency, deposition efficiency, cleansing efficiency, and a bar property such as skin abrasiveness, etc. based on changes from the baseline for these measurements using toilet bars without the inventive composition as quantified using the test methods described below. These skin benefit parameters can also be expressed quantitatively as the ratio of the inventive bar response to the comparative bar response. Where the magnitude of the inventive bar benefit improvement is expected to exceed the numerical result of the comparative bar, the observed ratio will be greater than 1.0; i.e. 1.02, 1.05, 1.07, 1.1, 1.2, 1.3, 1.4, 1.5, 1.6, 1.7, 1.8, 1.9, or 2.0. Where the magnitude of the inventive bar benefit improvement is expected to fall below the numerical result of the comparative bar, the observed ratio will be less than 1.0; i.e. 0.99, 0.98, 0.97, 0.95, 0.93, 0.90, 0.85, 0.80, 0.70, 0.60, 0.50, 0.40, 0.30, 0.20, or 0.10. Tables 1 to 4 below illustrate how various properties of the inventive bar are expected to compare to four different comparative bars. The test methods that may be used to measure the properties are provided below.

TABLE 1

Inventive bar vs. Comparative A[1] (Soap bar with exfoliants)

| Property | Ratio vs. Comparative A |
|---|---|
| Mildness | >1 |
| Moisturization | >1 |
| Moisturizer deposition | >1 |
| Softness | >1 |
| Smoothness | >1 |
| Skin abrasiveness [2] | <1 |

[1] Comparative A: True Blue Spa: Look Cool Minty Fresh Buffing Bar ® from Bath & Body Works containing: Sodium Palmitate, Sodium Cocoate, Water, Glycerin, Fragrance, Jojoba Wax, Pentasodium Pentetate, Tetrasodium etidronate, Gaultheria Procumbens (Wintergreen) Leaf Oil, Menta Piperita (Peppermint) Leaf Oil, TitaniumDioxide (C177891), Ultramarines (CI 77007)
[2] Higher value means worse.

TABLE 2

Inventive bar vs Comparative B[3] (Syndet bar without exfoliants)

| Property | Ratio vs. Comparative B |
|---|---|
| Exfoliation | >1 |
| Cleansing efficiency | >1 |
| Moisturizer deposition | =>1 |
| Softness | >1 |
| Smoothness | >1 |
| Bar sensory exfoliation | >1 |

[3] E.g. Dove ® Bar available from Unilever which contains Sodium Cocyl Isethionate, Stearic Acid, Sodium Tallowate, Water, Sodium Isethionate, Coconut Acid, Sodium Stearate, Cocamidopropyl Betaine, Sodium Cocoate, Fragrance, Sodium Chloride, Titanium Dioxide, Tetrasodium EDTA, Trisodium Etidronate, and BHT as indicated on the label.

TABLE 3

Inventive bar vs. Comparative C[4] (Syndet bar with exfoliants wherein more than 75% by weight of the particles have a particle size dimension along the major axis of less than 100 microns)

| Property | Ratio vs. Comparative C |
|---|---|
| Exfoliation[5] | >1 |
| Cleansing efficiency | >1 |
| Moisturizer deposition | =>1 |
| Softness[5] | >1 |
| Smoothness[5] | >1 |
| Bar sensory exfoliation | >1 |

[4] Example D (see below) except that the exfoliant is characterized by 75% by weight of the particles having a particle size dimension along the major axis of less than 100 microns.
[5] Clinical and/or consumer test (see method below).

TABLE 4

Inventive bar vs. Comparative D[6] (Syndet bar with exfoliants wherein more than 75% by weight of the particles have a particle size dimension along the major axis of greater than 600 microns)

| Property | Ratio vs. Comparative D |
|---|---|
| Moisturizer deposition | =>1 |
| Softness | >1 |
| Smoothness | >1 |
| Skin abrasiveness[7] | <1 |
| Bar sensory exfoliation | >1 |

[6] Example D (see below) except that the exfoliant is characterized by 75% by weight of the particles having a particle size dimension along the major axis of greater than 600 microns.
[7] Higher value means worse.

Surfactants:

Surfactants are an essential component of the inventive toilet bar composition. They are compounds that have hydrophobic and hydrophilic portions that act to reduce the surface tension of the aqueous solutions they are dissolved in. Useful surfactants can include anionic, nonionic, amphoteric, and cationic surfactants, and blends thereof.

Anionic Surfactants:

Synthetic Anionic Surfactants

The cleansing composition of the present invention contains one or more non-soap anionic detergents (syndets). Preferably the syndets have a zein value of 50 or less. Zein value may be measured using the test method described below.

The anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or aromatic sulfonates such as alkyl benzene sulfonate.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

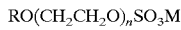

$$RO(CH_2CH_2O)_nSO_3M$$

wherein R is an alkyl or alkenyl having 8 to 18 carbons, preferably 12 to 18 carbons, n has an average value of greater than 1.0, preferably greater than 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glucosides and acyl isethionates, and the like.

Sulfosuccinates may be monoalkyl sulfosuccinates having the formula:

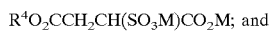

and amide-MEA sulfosuccinates of the formula;

wherein $R^4$ ranges from $C_8$–$C_{22}$ alkyl and M is a solubilizing cation.

Sarcosinates are generally indicated by the formula:

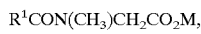

wherein $R^1$ ranges from $C_8$–$C_{20}$ alkyl and M is a solubilizing cation.

Taurates are generally identified by formula:

wherein $R^2$ ranges from $C_8$–$C_{20}$ alkyl, $R^3$ ranges from $C_1$–$C_4$ alkyl and M is a solubilizing cation.

The inventive toilet bar composition preferably contains $C_8$–$C_{14}$ acyl isethionates. These esters are prepared by reaction between alkali metal isethionate with mixed aliphatic fatty acids having from 6 to 12 carbon atoms and an iodine value of less than 20.

The acyl isethionate may be an alkoxylated isethionate such as is described in Ilardi et al., U.S. Pat. No. 5,393,466, titled "Fatty Acid Esters of Polyalkoxylated isethonic acid; issued Feb. 28, 1995; hereby incorporated by reference. This compound has the general formula:

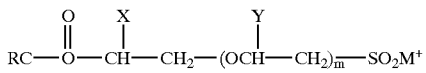

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In another embodiment of the inventive toilet bar, there is less than 5% by wt. of any of the following anionic surfactants: alkyl sulfates, alkyl sulfonates, alkyl benzene sulfonates, alkyl alkoxy sulfates, acyl taurides, acyl sulfates, and polyhydfroxy fatty acid amides either individually or of a blend thereof. Preferably there is less than 1%, and more preferably less than 0.1% by wt. of these surfactants.

Soaps.

The inventive toilet bar may contain soap, preferably it contains less than about 10.0% by wt. of soluble soap, more preferably it contains less than about 5% by wt. of soluble soap. The term "soap" is used herein in its popular sense, i.e., the alkali metal or alkanol ammonium salts of alkane- or alkene monocarboxylic acids. Sodium, potassium, mono-, di- and tri-ethanol ammonium cations, or combinations thereof, are suitable for purposes of this invention. In general, sodium, potassium, ammonium, mono-, di-, and tri-ethanol soaps of saturated C8–C14 alkyl chains and unsaturated fatty acids, preferably having C8–C22 alkyl chains, are soluble soaps.

Amphoteric Surfactants

One or more amphoteric surfactants may be used in this invention. Such surfactants include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

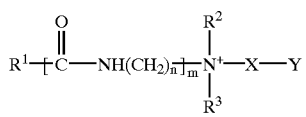

where $R^1$ is alkyl or alkenyl of 7 to 18 carbon atoms;
$R^2$ and $R^3$ are each independently alkyl hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric surfactants within the above general formula include simple betaines of formula:

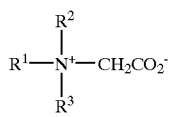

and amido betaines of formula:

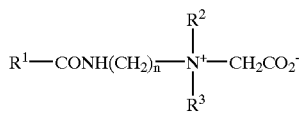

where n is 2 or 3.

In both formulae $R^1$, $R^2$ and $R^3$ are as defined previously. $R^1$ may in particular be a mixture of $C_{12}$ and $C_{14}$ alkyl groups derived from coconut oil so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

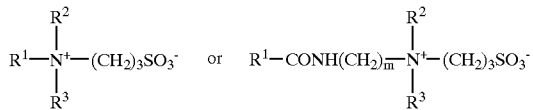

where m is 2 or 3, or variants of these in which —$(CH_2)_3SO_3^-$ is replaced by

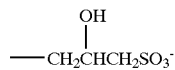

In these formulae $R^1$, $R^2$ and $R^3$ are as discussed previously.

Amphoacetates and diamphoacetates are also intended to be covered in possible zwitterionic and/or amphoteric compounds which may be used such as e.g., sodium lauroamphoacetate, sodium cocoamphoacetate, and blends thereof, and the like.

Nonionic Surfactants

One or more nonionic surfactants may also be used in the toilet bar composition of the present invention.

The nonionics which may be used include in particular the reaction products of compounds having a hydrophobic group and a reactive hydrogen atom, for example aliphatic alcohols, acids, amides or alkylphenols with alkylene oxides, especially ethylene oxide either alone or with propylene oxide. Specific nonionic detergent compounds are alkyl ($C_6$–$C_{22}$) phenols ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxide, and the like.

The nonionic may also be a sugar amide, such as a polysaccharide amide. Specifically, the surfactant may be one of the lactobionamides described in U.S. Pat. No. 5,389,279 to Au et al. titled "Compositions Comprising Nonionic Glycolipid Surfactants issued Feb. 14, 1995; which is hereby incorporated by reference or it may be one of the sugar amides described in U.S. Pat. No. 5,009,814 to Kelkenberg, titled "Use of N-Poly Hydroxyalkyl Fatty Acid Amides as Thickening Agents for Liquid Aqueous Surfactant Systems" issued Apr. 23, 1991; hereby incorporated into the subject application by reference.

Cationic Skin Conditioning Agents

An optional component in compositions according to the invention is a cationic skin feel agent or polymer, such as for example cationic celluloses. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200, and quaternary ammonium compounds such as alkyldimethylammonium halogenides.

A particularly suitable type of cationic polysaccharide polymer that can be used is a cationic guar gum derivative, such as guar hydroxypropyltrimonium chloride (Commercially available from Rhone-Poulenc in their JAGUAR trademark series). Examples are JAGUAR C13S, which has a low degree of substitution of the cationic groups and high viscosity, JAGUAR C15, having a moderate degree of substitution and a low viscosity, JAGUAR C17 (high degree of substitution, high viscosity), JAGUAR C16, which is a hydroxypropylated cationic guar derivative containing a low level of substituent groups as well as cationic quaternary ammonium groups, and JAGUAR 162 which is a high transparency, medium viscosity guar having a low degree of substitution.

Particularly preferred cationic polymers are JAGUAR C13S, JAGUAR C15, JAGUAR C17 and JAGUAR C16 and JAGUAR C162, especially Jaguar C13S. Other cationic skin feel agents known in the art may be used provided that they are compatible with the inventive formulation.

Other preferred cationic compounds that are useful in the present invention include amido quaternary ammonium compounds such as quaternary ammonium propionate and lactate salts, and quaternary ammonium hydrolyzates of silk or wheat protein, and the like. Many of these compounds can be obtained as the Mackine™ Amido Functional Amines, Mackalene™ Amido functional Tertiary Amine Salts, and Mackpro® cationic protein hydrolysates from the McIntyre Group Ltd. (University Park, Ill.).

In a preferred embodiment of the invention having a hydrolyzed protein conditioning agent, the average molecular weight of the hydrolyzed protein is preferably about 2500. Preferably 90% of the hydrolyzed protein is between a molecular weight of about 1500 to about 3500. In a preferred embodiment, MACKPRO™ WWP (i.e. wheat germ amido dimethylamine hydrolyzed wheat protein) is added at a concentration of 0.1% (as is) in the bar. This results in a MACKPRO™ WWP "solids" of 0.035% in the final bar formula for this embodiment.

Cationic Surfactants

One or more cationic surfactants may also be used in the inventive self-foaming cleansing composition.

Examples of cationic detergents are the quaternary ammonium compounds such as alkyldimethylammonium halogenides.

Other suitable surfactants which may be used are described in U.S. Pat. No. 3,723,325 to Parran Jr. titled "Detergent Compositions Containing Particle Deposition Enhancing Agents" issued Mar., 27, 1973; and "Surface Active Agents and Detergents" (Vol. I & II) by Schwartz, Perry & Berch, both of which are also incorporated into the subject application by reference.

In addition, the inventive toilet bar composition of the invention may include 0 to 15% by wt. optional ingredients as follows:

perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer) and the like; all of which are useful in enhancing the appearance or cosmetic properties of the product.

The compositions may further comprise antimicrobials such as 2-hydroxy-4,2',4'trichlorodiphenylether (DP300); preservatives such as dimethyloldimethylhydantoin (Glydant XL 1000), parabens, sorbic acid etc., and the like.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) and the like may be used advantageously in amounts of about 0.01% or higher if appropriate.

Humectants such as polyhydric alcohols, e.g. glycerine and propylene glycol, and the like; and polyols such as the polyethylene glycols listed below and the like may be used.

| Polyox WSR-205 | PEG 14M, |
| Polyox WSR-N-60K | PEG 45M, or |
| Polyox WSR-N-750 | PEG 7M. |

Moisturizers, also expressed as either humectants and emollients may be advantageously used in the present invention. The emollient "composition" may be a single benefit agent component or it may be a mixture of two or more compounds one or all of which may have a beneficial aspect.

In addition, the benefit agent itself may act as a carrier for other components one may wish to add to the inventive toilet bar.

Hydrophobic emollients, hydrophilic emollients, or a blend thereof may be used. Preferably, hydrophobic emollients are used in excess of hydrophilic emollients in the inventive toilet bar composition. Hydrophobic emollients are preferably present in a concentration greater than about 10% by weight most preferably greater than about 20% by wt. The term "emollient" is defined as a substance which softens or improves the elasticity, appearance, and youthfulness of the skin (stratum corneum) by either increasing its water content, adding, or replacing lipids and other skin nutrients; or both, and keeps it soft by retarding the decrease of its water content.

Useful emollients include the following:

(a) silicone oils and modifications thereof such as linear and cyclic polydimethylsiloxanes; amino, alkyl, alkylaryl, and aryl silicone oils;

(b) fats and oils including natural fats and oils such as jojoba, soybean, sunflower, rice bran, avocado, almond, olive, sesame, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin, and derivatives thereof;

(d) hydrophobic and hydrophillic plant extracts;

(e) hydrocarbons such as liquid paraffins, vaseline, microcrystalline wax, ceresin, squalene, pristan and mineral oil;

(f) higher fatty acids such as lauric, myristic, palmitic, stearic, behenic, oleic, linoleic, linolenic, lanolic, isostearic, arachidonic and poly unsaturated fatty acids (PUFA);

(g) higher alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils and extracts thereof such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, sesame, ginger, basil, juniper, lemon grass, rosemary, rosewood, avocado, grape, grapeseed, myrrh, cucumber, watercress, calendula, elder flower, geranium, linden blossom, amaranth, seaweed, ginko, ginseng, carrot, guarana, tea tree, jojoba, comfrey, oatmeal, cocoa, neroli, vanilla, green tea, penny royal, aloe vera, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins, minerals, and skin nutrients such as milk, vitamins A, E, and K; vitamin alkyl esters, including vitamin C alkyl esters; magnesium, calcium, copper, zinc and other metallic components;

(l) sunscreens such as octyl methoxyl cinnamate (Parsol MCX) and butyl methoxy benzoylmethane (Parsol 1789);

(m) phospholipids;

(n) antiaging compounds such as alpha hydroxy acids, beta hydroxy acids; and (o) mixtures of any of the foregoing components, and the like.

Preferred emollient benefit agents are selected from fatty acids, triglyceride oils, mineral oils, petrolatum, and mixtures thereof. Further preferred emollients are fatty acids.

Exfoliants

The inventive bar contains exfoliant particles that help remove dry skin. Not being bound by theory, the degree of exfoliation depends on the size and morphology of the particles, and their hardness. Large, rough and hard articles are usually very harsh and irritating. Very small particles that are very soft may not serve as effective exfoliants. Hardness is typically measured using the Moh scale. The Moh's scale of hardness is the method used to measure the ability of one substance to scratch another. The scale ranges in order of increasing relative hardness from 1 (softest) to 10 (hardest).

Common exfoliants used in the art include natural minerals such as silica, talc, calcite, pumice, tricalcium phopshate; seeds such as rice, apricot seeds, etc; crushed shells such as almond and walnut shells; oatmeal; polymers such as polyethylene and polypropylene beads, flower petals and leaves; microcrystalline wax beads; jojoba ester beads, and the like. These exfoliants come in a variety of particle sizes and morphology ranging from micron sized to a few mm. They also have a range of hardness. Some examples are given in table 5 below.

TABLE 5

| Material | Hardness (Mohs) |
| --- | --- |
| Talc | 1 |
| Calcite | 3 |
| Pumice | 4–6 |
| Walnut Shells | 3–4 |
| Dolomite | 4 |
| Polyethylene | ~1 |

The exfoliants in the present invention have particle sizes where at least 25% by weight of the particles (preferably at least 50%) have a major axis (i.e. the longest dimension of an irregularly shaped particle or the diameter of a spherical particle) in the range of about 100 to 600 microns; preferably about 100 to 300 microns, and most preferably where the smallest particle in this weight fraction has its major axis greater than 150 microns; and wherein the exfoliant particle has a hardness of less than about 4, or preferably less than about 3.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated. Physical test methods are described below:

The following inventive toilet bars may be formulated according to the manufacturing methods described below:

EXAMPLES A TO E (TABLES 6A AND 6B)

TABLE 6A

| Component | wt % | | |
|---|---|---|---|
| | A | B | C |
| Sodium cocyl isethionate | 32.0 | 25.0 | 49.8 |
| Stearic acid | 15.3 | 21.8 | 17.3 |
| Sodium tallowate/cocoate | 0.0 | 0.0 | 7.5 |
| Coconut fatty acid | 3.7 | 3.3 | 5.7 |
| Sodium isethionate | 7.1 | 5.0 | 5.1 |
| Water | 5.0 | 4.5 | 4.9 |
| Cocoamidopropylbetaine | 5.2 | 5.0 | 2.6 |
| Polyethylene glycol | 21.6 | 18.2 | 0.0 |
| Sodium stearate | 7.0 | 14.2 | 3.0 |
| Calcium sulfate | 0.0 | 0.0 | 0.0 |
| Sunflower seed oil | 0.0 | 0.0 | 1.0 |
| Petrolatum | 0.0 | 0.0 | 0.0 |
| Exfoliant | 0.1 | 0.1 | 0.1 |
| Minors | 3.0 | 3.0 | 3.0 |
| TOTAL | 100.0 | 100.0 | 100.0 |

TABLE 6B

| Component | wt % | |
|---|---|---|
| | D | E |
| Sodium cocyl isethionate | 49.7 | 40.2 |
| Stearic acid | 17.3 | 20.6 |
| Sodium tallowate/cocoate | 7.5 | 7.3 |
| Coconut fatty acid | 5.7 | 5.3 |
| Sodium isethionate | 5.1 | 3.6 |
| Water | 4.9 | 5.4 |
| Cocoamidopropylbetaine | 2.6 | 1.5 |
| Polyethylene glycol | 0.0 | 0.0 |
| Sodium stearate | 3.0 | 4.1 |
| Calcium sulfate | 0.0 | 7.9 |
| Sunflower seed oil | 1.0 | 0.0 |
| Petrolatum | 0.0 | 1.0 |
| Exfoliant | 0.2 | 0.2 |
| Minors | 3.0 | 3.0 |
| TOTAL | 100.0 | 100.0 |

Note:
Minors include fragrance, salts, preservatives, dyes and/or pigments, etc.

TABLE 7

| Formula | Exfoliant properties |
|---|---|
| A | polyethylene particles, 100–300 microns |
| B | microcrystalline wax, 250–600 microns |
| C | polyethylene particles, 100–300 microns |
| D | polyethylene particles, 100–300 microns |
| E | microcrystalline wax, 250–600 microns |

Method of Manufacture

Examples A to E are made as follows:
a) Vigorously mix above 85 C the ingredients listed in tables 6A and 6B for 30 minutes to 1 hour and 30 minutes until uniform, with the exception of the exfoliant, fragrance, and sunflower seed oil;
b) Cool the hot blend of ingredients rapidly using a chill roll;
c) Pelletize the product of step b;
d) Blend the exfoliant and sunflower seed oil; then, blend this mix of exfoliant and liquid moisturizers with the product of step c in a z-blade mixer to form the exfoliant preblend;
e) Blend the fragrance and the exfoliant pre blend in a ribbon blade mixer;
f) and, refine the product of step e once, then extrude and stamp the product into personal washing toilet bars.

Melt cast bars may also be made depending on the melt properties of the particular blend used. In this case all the bar ingredients, including exfoliants, are blended until uniform and finally at a temperature sufficient to render the blend flowable poured into a mold. The blend is then allowed to solidify under ambient or accelerated cooling conditions (such as refrigeration and the like).

DESCRIPTION OF TEST METHODS

Methods of Testing

One or more of the following tests can be used to characterize the inventive bar and compare it to comparative toilet bars.

a) Exfoliation Test:

A suitable corneocyte staining dye (eg: gentian violet) is applied to a 2–5 cm diameter spot on skin (arm/leg or any other part of the body as desired) and left on for 5 minutes to ensure uniform staining of the skin surface cells (corneocytes). The excess dye is then washed away by rinsing the spot under running water at 35 C for 30 secs with no rubbing of the skin.

The stained sites are then washed with the test product. For the bar the following wash method is adopted. Wet the spot on skin, pre-wet the bar, rub bar directly on spot for 30 secs (back and forth motion), rinse for 15 secs under running water at 35 C for 30 secs with no rubbing of the skin and gently pat dry. Allow the site to dry for 10 minutes. A d-squame tape (Cuderm® manufactured by CuDerm Corporation, (Dallas, Tex.) is applied on the washed spot under a uniform pressure for 30 secs and then removed. The d-squame tape is imaged using a Kodak DCS 420 digital camera with a 105 mm lens. The image is analyzed using Optimas image analysis software for area covered/total intensity of stained cells (Optimas® is available from Media Cybernetics, Silver Springs, Md.). By comparing this data to similar information from an unwashed site, one can estimate the amount of exfoliation caused by the test product as follows:

Exfoliation=(area of d-squame covered by stain on unwashed site−area of d-squame covered by stain on washed site)/(area of d-squame covered by stain on unwashed site)

Alternately exfoliation can also be evaluated in a consumer test as follows:

The test protocol consists of
1) Recruiting aprox. 10–20 women in the age group of 25–65 and who are complexion bar users.
2) Use test and comparative products for a week each. Half the panelists would use the test product first and the other half would use the comparative product first.
3) At the end of the test, the panelists rate their preference (on a 0–5 point scale) on the attribute of "exfoliation".

The degree of exfoliation is defined as the consumer rating on the 0–5 point scale b) Mildness Test:

i) Forearm Controlled Application Test (FCAT) Clinical Test Methodology

This controlled washing test is similar to that described by Ertel et al (A forearm controlled application technique for estimating the relative mildness of personal cleansing products, J. Soc. Cosmet. Chem., 46, 67 (1995)).

Subjects report to the testing facility for the conditioning phase of the study, which consists of using an assigned marketed personal washing cleanser for general use at home, up to four days prior to start of the product application phase. On Day 1 of the product application phase, a visual assessment is made to determine subject qualification. Subjects must have dryness scores >1.0 and erythema scores >0.5, and be free of cuts and abrasions on or near the test sites to be included in the product application phase. Subjects who qualify to enter the product application phase will then be instructed to discontinue the use of the conditioning product and any other skin care products on their inner forearms, with the exception of the skin cleansing test formulations that are applied during the wash sessions.

Qualified subjects will then have four 3.0-cm diameter (round) evaluation sites marked on each of the forearms using a skin safe pen (a total of eight sites). Visual evaluations for erythema and dryness will be conducted immediately prior to the first wash in each session and again in the afternoon of the final day (Day 5).

Washing Procedure for Bar Products

1. Both arms are washed simultaneously. Test sites are treated in a sequential manner starting with the site closest to the flex area, ending with the site proximal to the wrist.
2. The sites closest to the flex area of the inner forearm of both the right and left arm are moistened with warm water (90°–100° F.).
3. A moistened Masslinn towel is rubbed in a circular motion on a wetted test bar for approximately 6 seconds by studypersonnel which will result in 0.2–0.5 g of product to be dispensed.
4. The site is washed with the designated product for 10 seconds followed by a 90-second lather retention phase.
5. The above procedure (1–4) is then repeated for each of the test sites. Sites are then be rinsed (e.g. using a temperature of 35 C) for fifteen seconds and patted dry.
6. Upon completion the entire procedure is repeated (two washes/session).

For Liquid Products: A technician will prepare liquid products just prior to the wash session by dispensing between 0.1 g and 0.5 g of product either directly onto the skin or a moistened Maslinn towel or alternative application material. The washing procedure outlined above will then be used.

Evaluation Methods

Baseline visual assessments are made prior to the start of the product application phase, and immediately before each wash session thereafter, to evaluate dryness and erythema The final visual evaluation is conducted on the afternoon of the final day.

The 0–6 grading scale shown in Table 8 is used to assess the test sites for dryness and erythema. To maintain the evaluator's blindness to product assignment, visual assessments are conducted in a separate area away from the product application area.

TABLE 8

Eythema and Dryness grading scale.

| Grade | Erythema | Dryness |
|---|---|---|
| 0 | None | None |
| 1.0 | Barely perceptible | Patches of slight powderiness and redness occasional patches of small scales may be seen. Distribution generalized. |

TABLE 8-continued

Eythema and Dryness grading scale.

| Grade | Erythema | Dryness |
|---|---|---|
| 2.0 | Slight redness | Generalized slight powderiness. Early cracking or occasional small lifting scales may be present |
| 3.0 | Moderate redness | Generalized moderate powderiness and/or heavy cracking and lifting scales. |
| 4.0 | Heavy or substantial redness | Generalized heavy powderiness and/or heavy cracking and lifting scales |
| 5.0 | Extreme redness | Generalized high cracking and lifting scales. Powderiness may be present but not prominent. May see bleeding cracks. |
| 6.0 | Severe redness | Generalized severe cracking. Bleeding cracks. Bleeding cracks may be present. Scales large, may be beginning to disappear. |

Instrumental readings are taken on the first (baseline) and final day of the study.

Mildness of test product is calculated as 1/(mean change in dryness at end of the study)

In addition to visual evaluation, instrumental assessments of the treated sites will be conducted using an evaporimeter and skin conductance meter as described in the reference above.

ii) Patch Testing 48 hr continuous or 14 day cumulative insult patch test: In the 48 hr patch test 5–15% solution/slurry of the product is applied onto the upper arm/back of the subject using a standard cotton pad. Irritation response is recorded for up to 24 hrs after removal of the patch. In the 14 day cumulative test a 5–15% solution/slurry of the product is applied repeatedly every 24 hrs for 14 days. Irritation response is recorded for up to 24 hrs after removal of patch.

Mildness of test product is evaluated as 1/(mean erythema at 24 hr after final patch removal).

c. Moisturization Test:

Each outer, lower leg of a test subject will be divided into three sites, 2.5 by 2.5 inch squares (upper, middle and lower) for a total of 6 test sites per subject. One or two of the sites will be untreated and will be included in the randomization of products. A technician will treat the sites once or twice with the designated amount of test material for 10 seconds. Cleansing products will remain on the test sites for a maximum of 90 seconds. Sites will be rinsed for 30 seconds each (e.g. using a temperature of 35 C), ensuring that the test material from one site does not contaminate another site. After rinsing, the test sites are gently dried with a paper towel. The application consists of dosing with up to 5 different test materials on the designated sites, one material per test site, and one or two untreated sites. The study personnel will perform the following wash procedure:

Test Phase: Visual Evaluation

The scale as shown in Table 9 will be used to assess the test sites for dryness.

TABLE 9

| Grade | Dryness Scale | Erythema Scale |
|---|---|---|
| 0.0 | No dryness | No erythema |
| 0.5 | Perceptible dryness, fine white lines | |
| 1.0 | Fine dry lines, white powdery look and/or some uplifting flakes, on less than 30% of the test site | Mild erythema |

TABLE 9-continued

| Grade | Dryness Scale | Erythema Scale |
|---|---|---|
| 1.5 | More uniform flaking, covering 30–50% of the test site | |
| 2.0 | Uniform, marked flaking covering more than 50% of the test site area and/or isolated scaling | Moderate confluent erythema |
| 2.5 | Slight to moderate scaling | |
| 3.0 | Moderate to severe scaling with some uplifting of the scales | Marked erythema |
| 3.5 | Severe scaling and/or slight fissuring | |
| 4.0 | Severe scaling and severe fissuring | Deep erythema |

Baseline visual assessments will be made prior to the start of the product application phase and thereafter, immediately before each of the instrumental assessments, to evaluate skin dryness and erythema. One trained evaluator will conduct all visual evaluations during the product application phase. The evaluator will examine both lower legs with the aid of an illuminated magnifying lamp with a 3 diopter lens and a shadow-free circular cool white fluorescent light source.

Instrumental Assessment

All instrumental evaluations will be taken following a 30-minute acclimation period. The indoor humidity and temperature data will be recorded and included in the final report. Instrumental measurements may be taken at some or all of the following time points: 0, 1, 2, 4, 6, 8 and 24 hours after product application. Instruments to be used with this protocol include: ServoMed Evaporimeter with EP1 or EP2 probe, Corneometer CM820, the Skicon Skin Hygrometer with the MT-8C probe, and the Moisture Checker. The room temperature will be maintained at 68° to 77° F. and 30% to 40% Relative Humidity.

Moisturization is defined as mean change from baseline of (visual dryness or skin hydration).

d) Moisturizer Deposition Test:

Precondition the subject's skin (arms/legs) with non-moisturizer containing product for up to 2 days prior to testing. A baseline extraction is performed to estimate level of moisturizer (eg: fatty acids) present on the skin prior to product application. Controlled single application of product to skin (arms or legs) is made. For wash, bar is rubbed on skin for 30 secs and the lather left on for 90 secs, rinsed for 30 secs (e.g. using a temperature of 35 C) then gently pat dry. Following this, the site is extracted using a suitable solvent (IPA)/methanol 1:1). The extraction is performed as follows: A glass cup (3 cm diameter) is placed on the skin. 3 mls of solvent is placed into this and gently stirred with a glass rod for 2 minutes. The solvent is removed with a pipette. This step is repeated with a fresh 3 mls of solvent, to collect a total of 6 mls extract. The extracts are analyzed for stearic acid/palmitic acid content using either LC/MS or GC/MS, or the like.

e) Skin Abrasiveness Test

Skin abrasiveness is defined as consumer rated response of abrasivity on a 0–9 scale (0 means no abrasion, 10 is abrasivity caused by a pouf (i.e. a showering implement composed of thin plastic filaments, see also e.g. U.S. Pat. No. 5,650,384 to Gordon et al.).

This test is performed with 50 untrained consumers. They are asked to rate the abrasiveness of the test product on a 0–9 point scale. The data is normalized based on their response to a bar with no exfoliants which is assigned a value of zero and a pouf that is assigned a value of 9. The test products are applied to the flex area of the forearm by wetting the bar and rubbing back and forth 10–15 times.

f) Cleansing Efficacy Test

Model dirt (sebum/makeup—e.g. lipstick or mascara) is applied to a designated area on the forearm/face. The site is washed with the product. For wash, the bar is rubbed on skin for 1 minute, rinsed for 30 secs (e.g. using a temperature of 35 C), and gently pat dry. Amount of soil/makeup removed is estimated from the difference in the chromammeter readings using e.g. a Minolta Chromameter®, Model CM 2002 taken before and after wash. Alternately, high magnification digital mages are collected and analyzed using Optimas® software to quantitate the amount of soil/makeup removed during the wash.

Make Up Application:

Makeup will be applied to the 3.5×2.5 cm marked area on the inner side of the forearms in the manner consistent with its normal use. Cosmetic products are to be applied in a standardized way to ensure that approximately equal weights of make-up are transferred and that coverage of the test area is uniform. The application standards for the makeups are:

1.) Liquid make-up—20 µl pipette to the site and spread uniformly with gloved index finger.
2.) Lipstick—Three overlapping swipes.
3.) Eye Color Stick—Three overlapping swipes.
4.) Mascara—spread uniformly using spatula for even coverage.

Soil Application:

Soils will be applied to the 3.5×2.5 cm marked area on the inner side of the forearms in the manner described below and is specific to each individual study if soils are being used. The application techniques for the soils are:

1.) Grease—0.25 g–1.5 g. will be applied.
2.) Food—0.25 g–1.5 g. will be applied.
3.) Protein—0.25 g–1.5 g. will be applied.

Product Testing:

Baseline measurements will be performed using the Minolta Chromameter CM-2002. Make-up or Soil will then be applied to the delineated test sites as described above. Chromameter measurements will be taken again after the make up has dried for 10 minutes, then the make-up/soil will be removed. The standard washing procedure used to remove the make-up/soil is a 30-second wash with 0.5 cc of a liquid product with a 15-second rinse under running water using a suitable constant temperature (e.g. 35 C). When a towelette product is being used, the towelette is rubbed over the test site in a circular motion for 15 seconds. Final Chromameter measurement will be taken after the make-up/soil has been removed. This procedure may be performed twice a day for a period of up to 3 days. In repeat application studies visual assessments will be made for dryness and erythema using the standard visual grading scale as described above.

g) Skin Smoothness

Skin smoothness is evaluated (clinically) via Primos® (in-vivo optical skin topography measuring device supplied by GFM Esstezhnik GmbH, Berlin, Germany). Baseline roughness is measured (on leg/arms—starting dryness around grade 1–2). For wash, bar rubbed on skin for 30 secs and the lather left on for 90 secs, rinsed for 30 secs at 35 C. Measure again the roughness 30 minutes after wash process. This procedure may be performed twice a day for a period of up to 5 days.

Smoothness is defined as the mean decrease in roughness at end of study period. Alternately skin smoothness can also be evaluated in a consumer test as follows:

The consumer test protocol consists of:
1) Recruiting aprox. 10–20 women in the age group of 25–65 and who are complexion bar users.
2) Use test and comparative products for a week each. Half the panelists would use the test product first and the other half would use the comparative product first.
2) At the end of the test, the panelists rate their preference (on a 0–5 point scale) on the attribute of "Skin feels smoother".

Smoothness is defined as the consumer rating on the 0–5 point scale h) Skin Softness Skin softness may be evaluated using the Linear Skin Rheometer (Goodyear Scientific Instruments, UK). Exfoliated skin has less dry flakes—hence is more soft/less stiff. The test involves baseline skin rheometer readings (on the leg/arms) to measure the dynamic spring constant (mgf/mm) of skin which is related to skin stiffness/softness. For wash, the bar is rubbed on the skin for 30 secs and the lather left on for 90 secs, rinsed for 30 secs (at a suitable temperature e.g. 35 C), and the skin is gently pat dry. Next measure skin stiffness/softness 30 minutes after wash. This procedure may be performed twice a day for a period of up to 5 days. Softness is defined as the mean decrease in dynamic spring constant during the study period observed during the study period.

Alternately skin softness can also be evaluated in a consumer test as follows:

The test protocol consists of
1) Recruiting approx. 10–20 women in the age group of 25–65 and who are complexion bar users.
2) Use test and comparative products for a week each. Half the panelists would use the test product first and the other half would use the comparative product first.
3) At the end of the test, the panelists rate their preference (on a 0–5 point scale) on the attribute of "Skin feels softer".

Softness is defined as the consumer rating on the 0–5 point scale i) pH Test Method Form an aqueous slurry by blending 10 grams of the bar formula with 90 g of water to create a 10% slurry. The pH of the slurry is then measured at 25 C.

j) Zein Test Method

The cleansing base of the inventive toilet bar have zein solubilities of under about 50, 40, 30, and most preferably under about 25 using the zein solubility method set forth below. The lower the zein score, the milder the product is considered to be. This method involves measuring the solubility of zein (corn protein) in cleansing base solutions as follows:

0.3 g of cleansing base and 29.7 g of water are mixed thoroughly. To this is added 1.5 g of zein, and mixed for 1 hour. The mixture is then centrifuged for 30 minutes at 3000 rpm. After centrifugation, the pellet is extracted, washed with water, and dried in a vacuum oven for 24 hours until substantially all the water has evaporated. The weight of the dried pellet is measured and percent zein solubilized is calculated using the following equation:

$$\% \text{ Zein solubilized} = 100\,(1 - \text{weight of dried pellet}/1.5).$$

The % Zein is further described in the following references: E. Gotte, Skin compatibility of tensides measured by their capacity for dissolving zein protein, Proc. IV International Congress of Surface Active Substances, Brussels, 1964, pp 83–90.

h) Bar Sensory Exfoliation Index

The bar sensory exfoliation index is determined using the following procedure: The user takes the bar in one hand and rotates it under running water at 35 C. The number of rotations required for the exfoliant to be perceived (i.e. by tactile sensation) by the user is recorded. The bar exfoliation index is defined as the mean number of rotations required to perceive the exfoliant particles in the bar.

i) General Consumer Test Protocol

The test protocol consists of
1) Recruiting aprox. 10–20 women in the age group of 25–65 and who are complexion bar users.
2) Use test and comparative products for a week each. Half the panelists would use the test product first and the other half would use the comparative product first.
3) At the end of the test, the panelists rate their preference on a 0–5 point scale for the following attributes:

Exfoliates

Provides Gentle Exfoliation

Mositurizes and exfoliates

Skin feels softer

Skin feels smoother

Is good for dry skin

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A toilet bar comprising:
   a) a cleansing base including about 20 to 60% by wt. of one or more Syndet surfactants;
   b) about 10 to 50% by wt. of a moisturizer; and
   c) exfoliant particles wherein at least 25% by wt. of the particles have a particle size dimension along the major axis of the particle of from about 100 microns to about 600 microns.

2. The bar of claim 1 wherein the cleansing phase has a zein value of less than 50.

3. The bar of claim 1 wherein at least 50% of the exfoliant particles have a particle size dimension along the major axis of the particle of from about 100 to 300 microns.

4. The bar of claim 1 wherein the exfoliant particles have a hardness of less than about 4 Mohs.

5. The bar of claim 1 wherein the exfoliant particles have a hardness of less than about 3 Mohs.

6. The bar of claim 1 wherein the bar sensory exfoliation index is less than or equal to 10.

7. The bar of claim 1 wherein the exfoliant particles have a color distinct from the cleansing base.

8. The bar of claim 1 wherein the exfoliant particles are present in the bar at a concentration level of less than about 1% by wt.

9. The bar of claim 1 wherein the exfoliant particles greater than 400 microns are at a concentration level of less than about 0.25% by wt.

10. The bar of claim 1 wherein the exfoliant particles greater than 300 microns are at a concentration level of less than about 0.025% by wt.

11. The bar of claim 1 wherein the exfoliant particles are selected from polyethylene, microcrystalline wax, jojoba esters, amorphous silica, talc, tricalcium orthophosphate, or blends thereof.

12. The bar of claim 1 wherein the moisturizer is selected from fatty acids, triglycerides, mineral oil, petrolatum, glycerin, polyethylene glycol, or blends thereof.

13. The bar of claim 1 wherein the ratio of moisturizer to exfoliant is in the range of about 20:1 to 500:1.

14. The bar of claim 1 wherein the bar provides an aqueous slurry pH of about 4 to 8.

15. The bar of claim 1 further comprising less than about 10% by wt. of soluble soap.

16. A method for simultaneously exfoliating and moisturizing the skin comprising the steps of:
   a) providing a bar including
      i) a cleansing base including about 20 to 60% by wt. of one or more Syndet surfactants;
      ii) about 10 to 50% by wt. of a moisturizer;
      iii) exfoliant particles wherein at least about 25% by wt. of the particles have a particle size dimension along the major axis of the particle of from about 100 microns to 600 microns;
   b) adding sufficient water to wet the bar and the skin;
   c) applying the bar to the skin;
   d) rubbing the bar onto the skin for a time sufficient to remove dead skin cells and coat the underlying skin with at least one moisturizer.

17. A method for providing the user with a variable level of exfoliation and moisturization on different regions of the body, comprising the steps of:
   a) providing a toilet bar, wherein the bar includes
      i) a cleansing base including about 20 to 60% by wt. of one or more Syndet surfactants;
      ii) about 10 to 50% by wt. of a moisturizer; and
      iii) exfoliant particles wherein at least about 25% by wt. of the particles have a particle size dimension along the major axis of the particle of from about 100 microns to 600 microns.
   b) moistening the bar; the body or both;
   c) rubbing the bar on user selected areas of the skin for a time sufficient to remove dead skin cells where substantial exfoliation is desired;
   d) adding sufficient water to the bar to form a lather;
   e) rubbing the lather onto user selected areas of the skin where moisturization without substantial exfoliation is desired for a time sufficient to coat the underlying skin with at least one moisturizer; and,
   f) wherein steps (c) to (e) may be carried out in any sequence by the user.

* * * * *